United States Patent
Van Den Heuvel et al.

(10) Patent No.: US 10,619,028 B2
(45) Date of Patent: Apr. 14, 2020

(54) POLYARYLENE FIBER WITH IMPROVED HYDROLYTIC STABILITY

(71) Applicant: TEIJIN ARAMID B.V., Arnhem (NL)

(72) Inventors: Christiaan J. M. Van Den Heuvel, Ellecom (NL); Martijn Arnoldus Johannes Veld, Tilburg (NL); Joannes H. M. Quaijtaal, Arnhem (NL); René P. Verhoef, Ellecom (NL); Jorrit De Jong, Arnhem (NL); Wido Nijenhuis, Huissen (NL)

(73) Assignee: TEIJIN ARAMID B.V., Arnhem (NL)

( * ) Notice: Subject to any disclaimer, the term of this patent is extended or adjusted under 35 U.S.C. 154(b) by 0 days.

(21) Appl. No.: 15/744,720

(22) PCT Filed: Sep. 27, 2016

(86) PCT No.: PCT/EP2016/072919
§ 371 (c)(1),
(2) Date: Jan. 12, 2018

(87) PCT Pub. No.: WO2017/055247
PCT Pub. Date: Apr. 6, 2017

(65) Prior Publication Data
US 2018/0223077 A1    Aug. 9, 2018

(30) Foreign Application Priority Data
Sep. 29, 2015    (EP) ..................................... 15187383

(51) Int. Cl.
| | |
|---|---|
| *C08K 5/3462* | (2006.01) |
| *D01D 1/02* | (2006.01) |
| *D01F 1/10* | (2006.01) |
| *D01F 6/60* | (2006.01) |
| *C08L 77/10* | (2006.01) |
| *C07D 295/192* | (2006.01) |

(52) U.S. Cl.
CPC ........ *C08K 5/3462* (2013.01); *C07D 295/192* (2013.01); *C08L 77/10* (2013.01); *D01D 1/02* (2013.01); *D01F 1/10* (2013.01); *D01F 6/605* (2013.01); *D10B 2331/021* (2013.01)

(58) Field of Classification Search
None
See application file for complete search history.

(56) References Cited

U.S. PATENT DOCUMENTS

| | | | |
|---|---|---|---|
| 4,011,203 A | 3/1977 | Konomi et al. | |
| 4,530,952 A | 7/1985 | Tayama et al. | |
| 5,003,036 A | 3/1991 | Bowen et al. | |
| 5,091,456 A | 2/1992 | Rodini | |
| 5,543,492 A * | 8/1996 | Irwin ..................... | D01F 6/605 528/335 |
| 6,683,124 B2 | 1/2004 | Webster | |
| 2003/0111641 A1* | 6/2003 | Webster ............... | C08K 5/0041 252/301.35 |
| 2013/0157033 A1 | 6/2013 | Luo et al. | |

FOREIGN PATENT DOCUMENTS

| | | |
|---|---|---|
| EP | 0 643 039 A1 | 3/1995 |
| SU | 430556 A3 | 5/1974 |
| SU | 817038 A1 | 3/1981 |
| WO | 2010/094620 A1 | 8/2010 |

OTHER PUBLICATIONS

Nov. 9, 2016 International Search Report issued in International Patent Application No. PCT/EP2016/072919.

* cited by examiner

*Primary Examiner* — Robert T Butcher
(74) *Attorney, Agent, or Firm* — Oliff PLC

(57) ABSTRACT

A polyarylene fiber including 0.1-15% based on the weight of the fiber of an aromatic compound or a combination of aromatic compounds wherein each aromatic compound comprises an aromatic core and at least one of the substituents A or B, where A is represented by formula 1

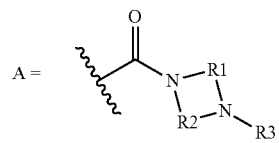

and B is represented by formula 2

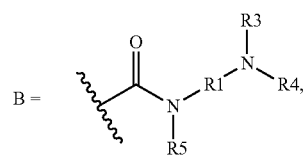

Also, a spin dope and a process for manufacturing a polyarylene fiber.

15 Claims, No Drawings

POLYARYLENE FIBER WITH IMPROVED HYDROLYTIC STABILITY

High strength, synthetic polymer materials are widely used in applications where durable high strength is required. During use articles comprising such synthetic polymers may be exposed to elevated temperatures, high humidity and/or water. Such conditions arise from the environment e.g. in tropical conditions, direct contact with water, machineries, human body or from heat generated during dynamic loading (hysteresis, internal/external friction). Such high performance synthetic materials include e.g. aramids and rigid rod aromatic heterocyclic polymers such as polybenzazole and others.

The environmental and use conditions can harm the strength of synthetic fibers. This is especially the case when fibers are exposed to conditions which favor hydrolysis, as e.g. extreme pH, presence of moisture and elevated temperature. Such conditions may occur for example in reinforced flexible flow lines, risers and umbilical pipes that are used in subsea oil and gas operations. It is believed that in particular synthetic polymers with carboxylate end groups are sensitive to deterioration when exposed to elevated temperature and high relative humidity.

For example, the residual strength of aromatic polyamide yarn at 70° C. and 50% relative humidity may be diminished after three years to 70% of the original value. For synthetic materials that have to be used for several years it is thus of importance to improve the durability.

An improvement of the hydrolytic stability of synthetic fibers has been described. U.S. Pat. No. 5,003,036 pertains to an aramid copolymer wherein at least 10% of the terephthaloyl monomers are replaced by mono- and/or di-chloroterephthaloyl groups. In U.S. Pat. No. 5,091,456 an aramid fiber was described comprising 0.5 to 3% of a specific fluoroalcohol additive. Improved strength retention was reported for such polymer. U.S. Pat. No. 5,543,492 is directed to an aramid comprising 2 to 8 mol % alkyl- and/or alkoxy-substituted diamine or diacid monomeric units. Also U.S. Pat. No. 4,011,203 describes an aramid copolymer comprising phenylenediamine, terephthaloyl and piperazine which has improved heat resistance, toughness and chemical resistance. In many of these references a copolymer is obtained by polymerizing p-phenylenediamine, terephthaloyl dichloride and a third monomer.

Disadvantages of introducing co-monomers are associated with their direct influence on the material properties, which often affect tensile properties of the copolymers relative to homopolymers. Moreover, high purity co-monomers, sometimes with complex molecular structures, need to be acquired or prepared for synthesis of the copolymers. The user is restricted in choosing the optimal polymer.

The object of the present invention is to obtain a polyarylene fiber with an improved hydrolytic stability and to overcome the limitations of the prior art. It is also an objective of the current invention to provide a fiber that combines high tensile strength and high modulus with good hydrolytic stability. Furthermore, this invention provides a spin dope and a process to obtain a polyarylene fiber with improved hydrolytic stability.

Surprisingly, it has now been found that the hydrolytic stability of polyarylene fibers can be much improved. This is achieved by a polyarylene fiber comprising 0.1-15% based on the weight of the fiber of an aromatic compound or a combination of aromatic compounds, characterized in that each aromatic compound comprises an aromatic core and at least one of the substituents A or B, where A is represented by formula 1:

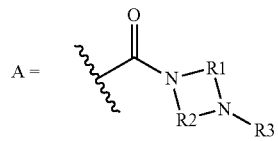

and B is represented by formula 2:

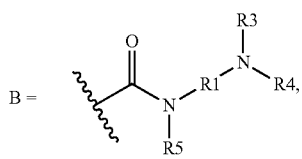

wherein R1 and R2 are independently of each other selected from an alkanediyl comprising 2 to 10 carbon atoms;

wherein R3 and R4 are independently of each other selected from —H, alkyl comprising 1 to 10 carbon atoms, homocycloalkyl comprising 3 to 10 carbon atoms or heterocycloalkyl comprising 1 to 10 carbon atoms;

wherein R5 is selected from: —H, alkyl comprising 1 to 10 carbon atoms, homocycloalkyl comprising 3 to 10 carbon atoms, heterocycloalkyl comprising 1 to 10 carbon atoms, and a carbonyl (—C(═O)— which forms a phthalimido ring structure fused to the aromatic core.

Basically, substituent A and B of the aromatic compound are carboxamides.

The present invention is directed to synthetic polyarylene polymer materials, more specifically lyotropic liquid crystal polymers, preferably polymers comprising phenylene groups, more preferably polymers selected from aramids (aromatic polyamides, polyaramids) and rigid rod aromatic polymers, more preferably rigid rod aromatic heterocyclic polymers. Rigid rod aromatic polymers have what are known in the art as rigid spacer segments. The rigid spacers often contain another cyclic unit, or functional end groups such as —NH—, —CO—, —O—, —COO—, —N═N—, and/or —CH═CH—. Generally, rigid rod polymers have highly para-oriented aromatic groups and the fibers made from these polymers have a high tensile modulus.

Many of these polymers are processed by using acidic solvents and they are therefore prone to hydrolytic instability.

The polyarylenes used for the polyarylene shaped fibers of the invention that can achieve a higher hydrolytic stability include aramids (aromatic polyamides) and rigid rod aromatic heterocyclic polymers such as polybenzazole, polyhydroquinone-diimidazopyridine and copolymers of these polymers.

In the context of the present specification aramid refers to an aromatic polyamide consisting of aromatic fragments directly connected to one another via amide fragments. Methods to synthesize aramids are known to those skilled in the art and typically involve the polycondensation of aromatic diamines with aromatic diacyl halides. Aramids may exist in the meta- and para-form, both of which may be used in the present invention. The use of aramid wherein at least 85% of the bonds between the aromatic moieties are para-aramid bonds is considered preferred. As typical members of this group are mentioned poly(para-phenylene terephthalamide), poly(4,4'-benzanilide terephthalamide), poly(para-phenylene-4,4'-biphenylene dicarboxamide) and poly(para-phenylene-2,6-naphthalene dicarboxamide), 5,4'-diamino-2-phenylbenzimidazole or poly(para-phenylene-co-3,4'-oxydiphenylene terephthalamide) or copolymers thereof. The use of aramid wherein at least 90%, more in particular at least 95%, of the bonds between the aromatic moieties are para-aramid bonds is considered preferred. The use of poly(para-phenylene terephthalamide), also indicated as PPTA, is particularly preferred.

Rigid rod aromatic heterocyclic polymers include polyazoles, such as polybenzazoles and polypyridazoles, and the like, they can be homopolymers or copolymers. Suitable polyazoles are polybenzazoles such as polybenzoxazole (PBO), polybenzothiazole (PBT), polybenzimidazole (PBI) and PBO-like polymers, as e.g. poly(p-phenylene-2,6-benzobisoxazole and polyhydroquinone-diimidazopyridine. Polybenzoxazole is a polymer containing an oxazole ring bonded to an aromatic group which is not necessarily a benzene ring. PBO-like polymers include a wide range of polymers each of which comprises a unit of a plurality of oxazole rings bonded to poly(phenylenebenzobisoxazole) and aromatic groups. PBI's and PBT's may have similar analogous structures.

If the polybenzazole is a polybenzimidazole, preferably it is poly[5,5'-bi-1H-benzimidazole]-2,2'-diyl-1,3-phenylene. If the polybenzazole is a polybenzothiazole, preferably it is a polybenzobisthiazole and more preferably it is poly(benzo[1,2-d:4,5-d']bisthiazole-2,6-diyl-1,4-phenylene. If the polybenzazole is a polybenzoxazole, preferably it is a polybenzobisoxazole and more preferably it is poly(benzo[1,2-d:4,5-d']bisoxazole-2,6-diyl-1,4-phenylene. In some embodiments the preferred polypyridazoles are rigid rod polypyridobisazoles including poly(pyridobisimidazole), poly(pyridobisthiazole), and poly(pyridobisozazole). The preferred poly(pyridobisozazole) is poly(1,4-(2,5-dihydroxy)phenylene-2,6-pyrido[2,3-d:5,6-d']bisimidazole.

Rigid rod aromatic heterocyclic polymers also include mixtures, copolymers or block polymers of two or more of the above.

The polyarylene fiber according to the invention comprises at least one of the above described polymers, it may also comprise a combination of such polymers. Usually, the polyarylene fiber comprises at least 60 wt % of any one or any combination of the polyarylenes used in the invention (based on the weight of the fiber).

In one embodiment, the polyarylene fiber comprises an aromatic compound having an aromatic core selected from: Core 1 (formula 3), Core 2 (formula 4) and Core 3 (formula 5)

Core 1

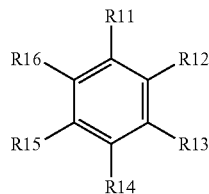

Formula 3

Core 2

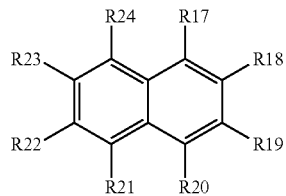

Formula 4

Core 3

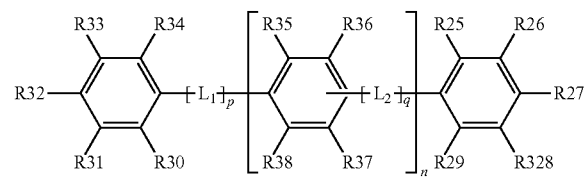

Formula 5 wherein R11, R12, R13, R14, R15, R16, R17, R18, R19, R20, R21, R22, R23, R24, R25, R26, R27, R28, R29, R30, R31, R32, R33, R34, R35, R36, R37 and R38 are independently of each other selected from the following monovalent radicals: an additional substituent A or B, —H, halogen, —NO$_2$, —CN, —OR3, —NR3R4, —SR3, alkyl comprising 1 to 10 carbon atoms, homocycloalkyl comprising 3 to 10 carbon atoms, heterocycloalkyl comprising 1 to 10 carbon atoms, perfluoroalkyl comprising 1 to 10 carbon atoms and a (substituted) carbonyl;

wherein L1 and L2 are each independently of each other selected from the following bi- and trivalent radicals: carbonyl (—C(=O)—), —O—, —S—, —SO$_2$—, alkanediyl comprising 1 to 6 carbon atoms, perfluoroalkanediyl comprising 1 to 6 carbon atoms, cycloalkanediyl comprising 3 to 10 carbon atoms, perfluorocycloalkanediyl comprising 3 to 10 carbon atoms, iminocarbonyl (—C(=O)NR5-, —R5NC(=O)—), acyloxy (—C(=O)O— or —OC(=O)—); and wherein p and q are 0 or 1 and n is 0, 1, 2, or 3.

Within the context of this invention the following terms are defined as follows: Alkyl means a monovalent saturated linear or branched hydrocarbyl radical with 1 to 10 carbon atoms.

Alkanediyl means a bivalent saturated linear or branched hydrocarbyl radical with 2 to 10 carbon atoms.

Heterocycloalkyl means a non-aromatic monovalent monocyclic or polycyclic radical with 1 to 10 carbon atoms and at least one heteroatom chosen from N, O, S. A heterocycloalkyl group can have one or more carbon-carbon double bonds or carbon-heteroatoms double bonds in the ring as long as the ring is not rendered aromatic by their presence.

Homocycloalkyl means a monovalent saturated cyclic hydrocarbyl radical with 3 to 10 carbon atoms.

Perfluoro- means that all hydrogen atoms in the corresponding fragment have been substituted by fluorine atoms.

A carbonyl group is a group —(C=O)—. This includes substituted carbonyl groups. Examples of substituted carbonyl groups are: esters (—C(=O)O—), amides (—C(=O)N—), ketones (—C(=O)C—), aldehydes (—C(=O)H), and carboxylic acid (—C(=O)OH). In one embodiment adjacent carbonyl substituents may form a phthalimide fragment. An alkoxy moiety has the formula —OR3. A thioalkyl substituent has the formula —SR3. Substituted amines are represented as —NR3R4 and a phthalimido ring structure is a fragment of formula 6 where the aromatic ring represents the aromatic core of the aromatic compound. The phthalimido fragment can be formed from substituent B by the addition of a second carbonyl group at position R5 with N being further substituted as described for substituent B. Alternatively, the phthalimido fragment can be part of fragment L1 or L2 of Core3.

Formula 6

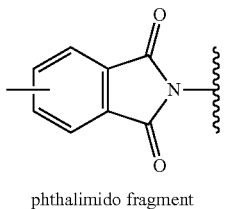

phthalimido fragment

Various methods to form a phthalimide fragment are known by those skilled in the art. Phthalimides are typically formed by dehydration of adjacent carboxamide (—C(=O)NHR—) and carboxylic acid (—C(=O)OH) fragments.

One or multiple non-adjacent carbon atoms of the alkyl and alkanediyl substituents of the compound according to the invention can be substituted by heteroatoms (N, O, S) to give secondary amine, ether and thioether fragments, respectively. In such an embodiment the total number of atoms of the backbone is not increased but instead one of the carbons is replaced by a heteroatom.

One or multiple hydrogen atoms on the alkyl, alkanediyl or cycloalkyl substituents can be substituted with halogens or heteroatoms (—NR3R4, —OR3, —SR3, where R3 is H) to give (substituted) amines, alcohols and thiols (where R3 is an alkyl), respectively.

If L1 or L2 comprises an aliphatic moiety said moiety can be linear or branched.

Generally, the substituents R (R1-R38) of each compound according to this invention are chosen to increase the hydrophobicity of the compound.

In a preferred embodiment at least one of the compounds used in the polyarylene shaped bodies of present invention is substituted with at least one substituent A wherein R1 and R2 of said substituent A are —C₂H₄—

Independently, or in combination with this embodiment, R3 of said substituent A is methyl.

In a preferred embodiment the polyarylene fiber according to this invention comprises an aromatic compound with substituent B wherein R1 of said substituent B is —C₂H₄—.

Independently, or in combination therewith, R3 and R4 of said B are methyl.

Independently, or in combination with such R1, such R3 and such R4, R5 of said B is preferably hydrogen.

In a preferred embodiment, the polyarylene fiber comprises at least one aromatic compound having a Core 3, where L1 and L2 are each an iminocarbonyl group where n, p and q are 1. This embodiment can also occur in combination with the herefore stated embodiments.

Preferred is thus a polyarylene fiber wherein substituent A of the aromatic compound is a carboxamide derived from an 1-alkylpiperazine, preferably from 1-methylpiperazine.

In another preferred embodiment substituent B of the aromatic compound is a carboxamide derived from an N,N-dialkylethylenediamine.

In another preferred embodiment an aromatic compound consisting of Core1, Core2 or Core3 is used wherein the substituents R11, R12, R13, R14, R15, R16, R17, R18, R19, R20, R21, R22, R23, R24, R25, R26, R27, R28, R29, R30, R31, R32, R33, R34, R35, R36, R37 and R38 are independently of each other selected from hydrogen or halogen.

A compound used in this invention may e.g. be:

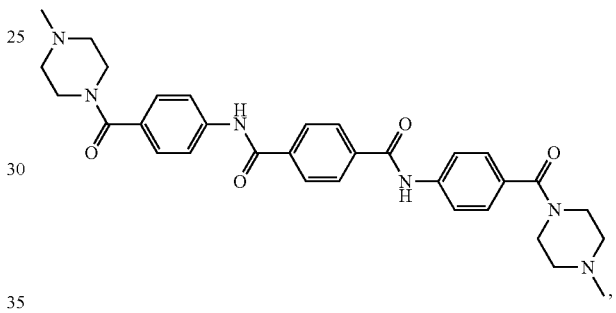

N¹,N⁴-bis[4-(4-methylpiperazine-1-carbonyl)phenyl]benzene-1,4-dicarboxamide

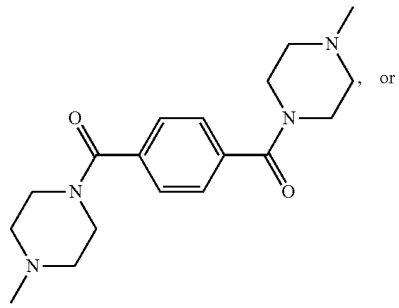

1-methyl-4-[4-(4-methylpiperazine-1-carbonyl)benzoyl]piperazine

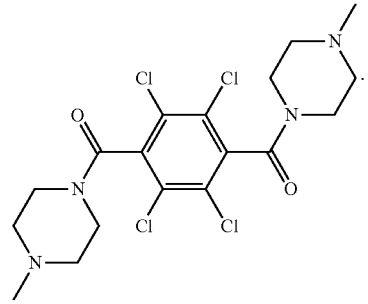

1-methyl-4-[2,3,5,6-tetrachloro-4-(4-methylpiperazine-1-carbonyl)-benzoyl]piperazine Other non-limitative examples include:

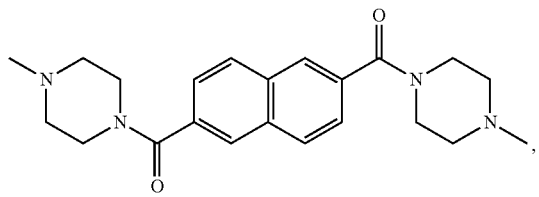

1-methyl-4-[6-(4-methylpiperazine-1-carbonyl)naphthalene-2-carbonyl]piperazine

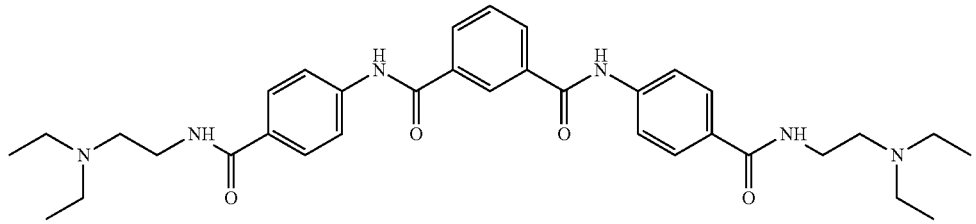

1-N,3-N-bis(4-{[2-(diethylamino)ethyl]carbamoyl}phenyl)benzene-1,3-dicarboxamide

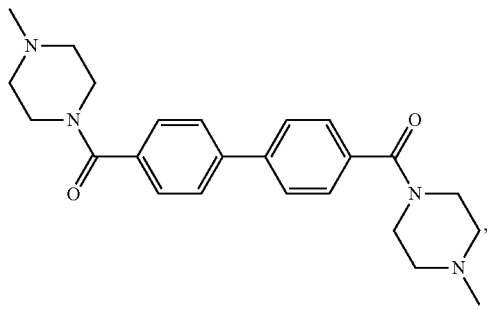

1-methyl-4-{4-[4-(4-methylpiperazine-1-carbonyl)phenyl]benzoyl}piperazine

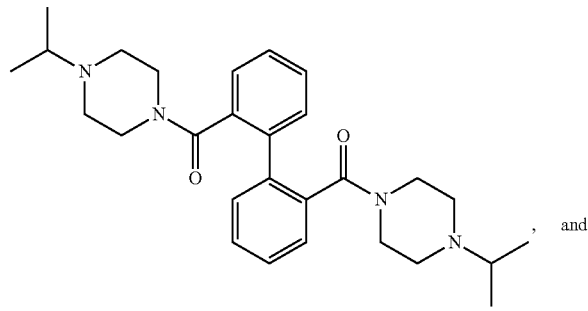

1-(propan-2-yl)-4-(2-{2-[4-propan-2-yl)piperazine-1-carbonyl]phenyl}benzoyl)piperazine, and

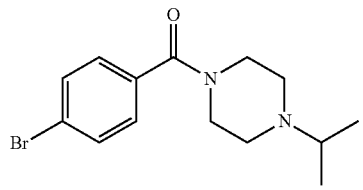

1-(4-bromobenzoyl)-4-(propan-2-yl)piperazine

The aromatic compounds comprising fragment A or fragment B used in the invention are chemically inert in the sense that the polyarylene polymer and the added aromatic compound do form an admixture.

That means, that if an aromatic compound comprising fragment A or fragment B would be present during the polymerization reaction the compound does not function as a monomer which is built into the polymer. Therefore, in the present invention no copolymer is formed but a composition comprising a polyarylene polymer and the compound or combination of compounds.

In order to prevent that the original color of the fiber changes by the introduction of the neutralizing aromatic compound, the aromatic compound should preferably not be a pigment or colorant. Pigments and colorants are known additives, but do usually not offer the advantageous effect on the hydrolytic stability as do the aromatic compounds used in present invention.

The amount of compound or combination of compounds in the polyarylene fiber is chosen based on the molecular weight of the compound.

The total concentration of a compound or a combination of compounds in the polyarylene fiber varies between 0.1 and 15 wt % based on the weight of the polyarylene fiber, preferably 1-10 wt %, more preferably 2-6 wt %.

Preferably, any compound used in the invention has a molecular weight between 200 and 1000 g/mol, preferably between 300 and 800 g/mol, more preferably, between 400 and 600 g/mol.

For purposes herein, the term "fiber" is defined as a flexible, macroscopically homogeneous body. Fibers have a high ratio of length to the width of the cross-sectional area perpendicular to that length. The fiber cross section can have any shape, e.g. round or rectangular. The term "fiber" according to present invention includes but is not limited to filaments (including monofilaments and multifilament bundle), continuous yarn, tapes, pulp, fibrils, fibrids, staple fiber and short cut. In the present invention, a tape is defined as an object of which the length, i.e., the largest dimension of the object, is larger than the width, the second smallest dimension of the object, and the thickness, i.e., the smallest dimension of the object, while the width is in turn larger than the thickness. More in particular, the ratio between the length and the width generally is at least 2. Depending on the tape width the ratio may be larger, e.g., at least 4, or at least 6. The maximum ratio is not critical to the present invention and will depend on processing parameters.

The polyarylene fiber according to the invention also encompasses embodiments where the fiber comprises different polyarylene polymers as defined above. For example, a fiber according to the invention may comprise aramid filaments and filaments made of rigid rod aromatic heterocyclic polymer, where either one or both of the aramid filaments and rigid rod aromatic heterocyclic polymer filaments comprises an aromatic compound according to the current invention.

The polyarylene fiber according to the invention can be used in a wide variety of products.

Examples include reinforced pipes for oil/gas transport or city heating, umbilicals, ropes, cables, slings, cooling hoses in cars, tires, conveyor belts and penetration-resistant articles, as e.g. antiballistic or cut-protective articles.

One objective of this invention is to provide a polyarylene fiber with improved hydrolytic stability. The hydrolytic stability relates to the breaking tenacity which remains after the fiber has been exposed to conditions that result in hydrolysis. The hydrolytic stability is determined by measuring the breaking tenacity and determining the time point and period of time when 90% (t0.9) or 80% (t0.9) of the original breaking tenacity remains under the prescribed temperature and low pH conditions. Thus the period of time when a fiber, having been exposed to the prescribed temperature (90° C.) and low pH (pH 4) conditions for said time, has 90% (t0.9) or 80% (t0.8) of the breaking tenacity compared to a fiber which has been exposed to standard environmental conditions (air, 20° C., 65% relative humidity). For tapes the same method can be applied. A film can be cut into tapes, which can subsequently be measured in the same way.

The polyarylene fiber according to this invention preferably has a hydrolytic stability t0.9 of at least 3 weeks, preferably at least 6 weeks, more preferably at least 9 weeks and even more preferably at least 12 weeks and a hydrolytic stability t0.8 of at least 10 weeks, preferably at least 15 weeks, more preferably at least 20 weeks and even more preferably at least 25 weeks, wherein the hydrolytic stability t0.9 is defined as the period of time until the breaking tenacity of the fiber when being exposed to a solution of pH 4 and 90° C. amounts to 90% compared to the breaking tenacity of the fiber when being exposed to air having a temperature of 20° C. and 65% relative humidity. The hydrolytic stability t0.8 is defined as the period of time until the breaking tenacity of the fiber when being exposed to a solution of pH 4 and 90° C. amounts to 80% compared to the breaking tenacity of the fiber when being exposed to air having a temperature of 20° C. and 65% relative humidity.

A detailed description of the method for determining the hydrolytic stability is given in the experimental section, but applicable to the invention in general.

The fiber having 100% breaking tenacity is the same fiber as the fiber exposed to hydrolytic conditions and thus comprises the same aromatic compound or combination of compounds.

Thus, e.g. the polyarylene fiber according to the invention may be exposed to environmental conditions of 90° C. and pH 4 for 3 weeks and the breaking tenacity of the fibers remains 90% compared to the breaking tenacity of a polyarylene fiber being exposed to standard environmental conditions.

The breaking tenacity is determined according to ASTMD7269 after conditioning the fiber at 20° C. and 65% relative humidity for 14 hours in accordance with ASTMD1776.

The hydrolytic stability t0.9 of compositions without the compounds described in current invention is usually less than 3 weeks and the hydrolytic stability t0.8 is less than 10 weeks, and generally cannot reach values as achieved by the present invention. In one embodiment the hydrolytic stability t0.9 of the polyarylene fiber of present invention is increased by at least 50%, preferably at least 100%, more preferably at least 200% (in weeks, compared to the hydrolytic stability of a polyarylene fiber comprising none of the described compounds).

This invention is also directed to a process to manufacture a polyarylene fiber with improved hydrolytic stability. This process comprises the following steps:

i) preparing a composition comprising polyarylene polymer, a solvent and an aromatic compound or combination of aromatic compounds, ii) processing the composition to obtain the polyarylene fiber, characterized in that each aromatic compound comprises at least one of the substituents A or B, where A is represented by formula 1

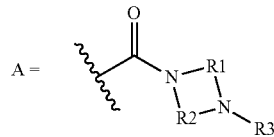

and B is represented by formula 2

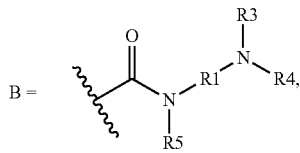

wherein R1 and R2 are independently of each other selected from an alkanediyl comprising 2 to 10 carbon atoms;

wherein R3 and R4 are independently of each other selected from —H, alkyl comprising 1 to 10 carbon atoms, homocycloalkyl comprising 3 to 10 carbon atoms or heterocycloalkyl comprising 1 to 10 carbon atoms;

wherein R5 is selected from: —H, alkyl comprising 1 to 10 carbon atoms, homocycloalkyl comprising 3 to 10 carbon atoms, heterocycloalkyl comprising 1 to 10 carbon atoms, and a carbonyl (—C(=O)— which forms a phthalimido ring structure fused to the aromatic core.

The composition may be processed in a number of ways.

It may be processed into fibers which can subsequently be processed into tapes. To obtain the fibers of the invention, conventional spinning methods well-known to the expert can be used, as e.g. wet spinning, preferably air-gap wet spinning.

However, it is also possible to apply jet spinning, where an air or coagulant stream hits the dope stream and diverts it into droplets. Another processing method is rotor spinning, where spin dope is introduced into a rotor turning at high velocity, squeezed out via small holes, and coagulated on a wall with flowing coagulant (rotor-stator coagulation). With jet spinning and rotor spinning it is possible to directly obtain pulp, fibrils and fibrids.

Conventional wet spinning comprises the following steps: spin dope preparation, filtration, spinning, coagulation, washing, neutralizing and drying. Such a process is well-known and has been described in for example WO2010094620.

The composition comprising solvent, polyarylene polymer and an aromatic compound or combination of aromatic compounds can be prepared in different ways. In one embodiment the polymer, solvent and aromatic compound or combination of aromatic compounds is mixed. However, it is also possible to add an aromatic compound or combination of aromatic compounds during the polymerization reaction which yields the polyarylene.

The solvent is chosen in dependence of the chosen polymer. For example, for para-aramid usually sulfuric acid is used, while for polybenzazoles phosphoric acid may be used.

Preferably, after processing the polyarylene fiber is heated at a temperature between 250 and 500° C., preferably a temperature between 300 and 450° C., more preferably between 350 and 400° C. . The duration of the heat treatment can vary from subseconds to minutes, or even longer in case of off line heat treatment. Preferably, tension is applied during heating.

In a preferred embodiment the heat treatment is applied by using a contactless oven flushed with nitrogen.

Thus, preferably, in the process of current invention the fiber obtainedafter step ii) is heated at a temperature between 250 and 500° C., preferably a temperature between 300 and 450° C., more preferably a temperature between 350 and 400° C.

The heat treatment may induce crystal growth which may have an additional positive effect on the hydrolytic stability. The crystal size growth can be determined by measuring the apparent crystal size L110 by wide angle X-ray diffraction.

For example, L110 values of an aramid fiber ranging between 45 and 130 Å, preferably between 60 and 120 Å, more preferably between 80 and 110 Å are considered especially advantageous. Therefore, the current invention is also directed to an aramid fiber according to the invention with a crystal size L110 ranging between 45 and 130 Å, preferably between 60 and 120 Å, more preferably between 80 and 110 Å.

For example, L110 values of polybenzazole fiber ranging between 55 and 130 Å, preferably between 65 and 125 Å, more preferably between 80 and 120 Å are considered especially advantageous. Therefore, the current invention is also directed to a polybenzazole fiber according to the invention with a crystal size L110 ranging between 55 and 130 Å, preferably between 65 and 125 Å, more preferably between 80 and 120 Å.

Where spinning processes are used to manufacture the polyarylene fiber, a spin dope has to be prepared.

Therefore, current invention is also directed to a spin dope comprising polyarylene polymer and 0.1 to 15% based on the weight of polyarylene polymer in the spin dope of an aromatic compound or a combination of aromatic compounds, characterized in that each compound comprises an aromatic core and at least one of the substituents A or B, where A is represented by formula 1

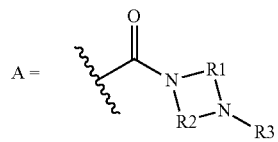

and B is represented by formula 2

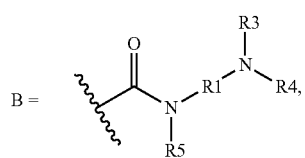

wherein R1 and R2 are independently of each other selected from an alkanediyl comprising 2 to 10 carbon atoms;

wherein R3 and R4 are independently of each other selected from —H, alkyl comprising 1 to 10 carbon atoms, homocycloalkyl comprising 3 to 10 carbon atoms or heterocycloalkyl comprising 1 to 10 carbon atoms;

wherein R5 is selected from: —H, alkyl comprising 1 to 10 carbon atoms, homocycloalkyl comprising 3 to 10 carbon atoms, heterocycloalkyl comprising 1 to 10 carbon atoms, and a carbonyl (—C(=O)— which forms a phthalimido ring structure fused to the aromatic core.

For para-aramid, especially PPTA, the solvent of such a spin dope is sulfuric acid. For polybenzazoles this is usually phosphoric acid. Preferably, the compounds described in current invention are stable in the acidic solvents and not or only slightly soluble in aqueous solutions so that no or only low levels of the compound are washed-out during or after coagulation.

When the polyarylene is aramid, the aramid concentration based on the weight of the spin dope varies between 12 and 25 wt %, preferably between 17 and 22 wt %. Most preferred is an aramid concentration between 18 and 20 wt %.

Either one aromatic compound or a combination of aromatic compounds as described above are present in the spin dope. The total concentration of a compound or a combination of compounds varies between 0.1 and 15 wt % based on the weight of the aramid in the spin dope, preferably, 1-10 wt %, more preferably 2-6 wt %.

If multiple compounds are used, the concentration of the combination (determined by adding the single concentration values) shall be in the range of the above cited concentrations.

The different embodiments described for compounds which can be comprised in the polyarylene fiber are also possible embodiments of the compound or combination of compounds used in the spin dope and in the process to produce an polyarylene fiber.

More specifically, the invention also relates to a spin dope comprising the polyarylenes and aromatic compound(s) as defined in claims 2-13 and to a process wherein polyarylenes and aromatic compounds are used as defined in claims 2-13.

The following examples describe the invention in more detail but by no means limit the scope of the invention.

EXPERIMENTAL DETAILS AND EXAMPLES

1. Determination of Linear Density and Tensile Properties

The mass per unit (linear density) of the yarns is measured by weighing a known length of the yarn according to ASTM D1907 "Test Method for Linear Density of Yarn (Yarn Number) by the Skein Method". The unit of linear density is dtex=g/10000 m, or 0.1 mg/m.

The tensile properties of the yarns are determined in accordance with ASTM D7269 "Standard Test Methods for Tensile Testing of Aramid Yarns" thereby conditioning the samples at 20° C. and 65% relative humidity for 14 hours in accordance with ASTM D1776 "Practice for Conditioning and Testing Textiles". Different from this standard, no preconditioning at 45° C. during 3 hours was applied. In analogy the linear density and tensile properties of tapes are measured be it that these samples are not twisted.

2. Determination of Hydrolytic Stability

The hydrolytic stability of the yarns is determined in ovens with forced air circulation. Yarns provided with protective twist are wound tensionless on a glass rod and placed in a glass tube filled with a pH4 buffer solution based on citric acid, sodium hydroxide and hydrochloric acid. After insertion the glass tube is closed and placed in the oven at 90° C. At regular time intervals samples are removed from the oven. After cooling, the yarn is rinsed with tap water and dried for 3 hours at 45° C. After drying the yarn is conditioned for at least 14 hours at 20° C. and 65% R.H.

The breaking tenacity is measured according to ASTM D7269. The breaking tenacity of the sample being exposed to hydrolytic conditions is expressed as percentage relative to the breaking tenacity of a sample of the same yarn wound on a glass rod and being exposed to air having a temperature of 20° C. and 65% relative humidity. The breaking tenacity of the air-exposed yarn is set to 100%.

Typically the breaking tenacity is measured after 1, 2, 4, 8, 13, 26 and 52 weeks of exposure.

By interpolation the time is determined in which the breaking tenacity of the yarn is reduced to 90% (t0.9) and 80% (t0.8) of the initial value.

3. Determination of the Lateral Crystal Size a) Sample Preparation and Measurement The sample, in this instance the aramid fiber sample, is measured using a Bruker D8 Advance diffractometer in θ/2θ geometry. The diffractometer is equipped with parallel beam optics and point detector (scintillation counter). The optics consists of a primary 60 mm Göbel focusing mirror (a parabolic Ni/C multilayer device) providing Cu—Kα radiation (Kα1/Kα2 doublet, Kα wavelength=1.5418 Å), and 0.12° Soller slits.

The yarn sample is wound on a sample holder with a thickness of 0.3 mm, making sure that the filaments are parallel. The sample holder is mounted in the diffractometer with the yarn axis parallel to the goniometer axis. For the determination of the crystallite size the equatorial X-ray scattering intensity with the 110 and 200 equatorial reflections are measured as function of the diffraction angle 2θ in reflection geometry. The generator settings are 40 kV, 35 mA. Scan parameters: range 3-43° (2θ), step size: 0.02° (2θ), time/step: 8 sec. The diffraction angle 2θ is the angle between the primary X-ray beam and the diffracted X-ray beam.

b) Evaluation

The crystallite size as quantified via the L110 parameter is inversely proportional to the peak width β of the 110 reflection according to Scherrer's formula:

$$L_{110} = \frac{\lambda(180/\pi)}{\cos\theta\sqrt{\beta^2 - \beta_{corr}^2}}$$

where:

λ Is the wavelength of the X-rays employed (1.5418 Å).

θ is half the diffraction angle $\beta_{corr}$ is the instrumental broadening in degrees The full width at half maximum β (FWHM) of the left hand main peak is determined using profile fitting. The left hand main peak is the 110 reflection. In the profile fitting the 110 and 200 peaks are fitted together with a linear background. The peaks are fitted with a symmetrical Pearson VII function. Use the instrumental broadening obtained by measuring a silicon powder sample. The peakwidth (FWHM) of the peak at approximately 2θ=28° is taken as the instrumental broadening $\beta_{corr}$. The crystallite size parameter L110 is subsequently calculated according to the Scherrer formula. For polybenzazoles an analogous procedure is used to determine the crystallite size L of the main equatorial peak at 2θ=16.2°.

4. Synthesis of Compounds Used in the Invention a) Synthesis of $N^1,N^4$-bis[4-(4-methylpiperazine-1-carbonyl)phenyl]benzene-1,4-dicarboxamide (1)

A synthetic route towards compound 1 is shown in scheme 1 and consists of three consecutive reaction steps a1-a3 that are each described below.

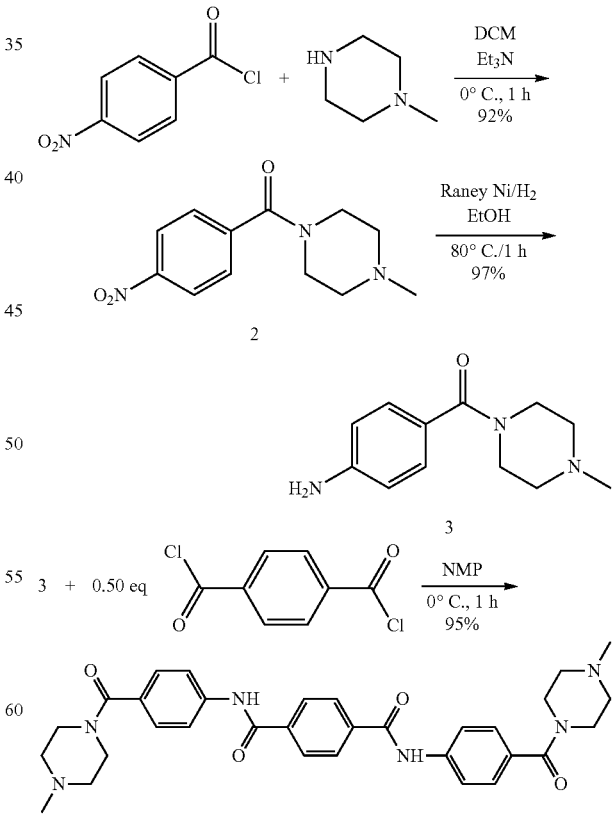

Scheme 1 a1) Synthesis of (4-methylpiperazin-1-yl)(4-nitrophenyl)methanone (2)

A 100 mL 3-necked flask was equipped with a magnetic stirrer bar, nitrogen in- and outlet and septum. The setup was thoroughly dried using a heat gun and allowed to cool to room temperature under a nitrogen flow. Then, 4-nitrobenzoyl chloride (4.64 g, 25.0 mmol) was dissolved in dry dichloromethane (50 mL) and the solution was 10 minutes in an ice-water bath. N-methylpiperazine (2.58 g, 25.8 mmol, 1.03 eq) was added drop wise over a 10 minute time interval while stirring vigorously. The resulting suspension was stirred for 1 hour at 0° C., after which triethylamine (5.01 g, 50.0 mmol, 2.0 eq) was added and stirrring was continued at r.t. for 1 h. The reaction mixture was transferred into a separatory funnel and washed with demineralized water (3×50 mL). The organic layer was dried over $Na_2SO_4$, filtered over a paper filter and all volatiles were removed under reduced pressure using a rotary evaporator to give the desired product as a pale orange solid (5.77 g 23.1 mmol, 92%).

a2) Synthesis of (4-methylpiperazin-1-yl)(4-aminophenyl)methanone (3)

(4-methylpiperazin-1-yl)(4-nitrophenyl)methanone (2) was catalytically reduced using Raney Nickel as catalyst in a 0.5 L Büchi autoclave. The reactor was charged with a solution of nitro compound 2 (25.2 g, 101.1 mmol) in 96% ethanol (249.2 g) and a suspension of Raney Nickel (2.05 g, 0.22 mass eq.) in water (9 mL). The reactor vessel was subsequently purged with purged with $N_2$ (3×) and $H_2$ (3×) after which the reactor contents were heated to 80° C. and the reactor was pressurized to 10 bar. The stirring rate was increased to 1500 rpm and the reaction was allowed to proceed for 60 minutes to assure complete reduction. The reactor contents were cooled to 50° C., and the reactor was emptied into a vessel through a filter (2 μm pore size). Directly afterwards, another amount of nitro compound 2 (21.0 g) in 96% ethanol (210 g) was reduced using the same batch of catalyst. After removal of the second batch, the reactor was rinsed with ethanol (130 g) and all volatiles of the combined fractions were removed under reduced pressure using a rotary evaporator to give a pink to pale brown oil that crystallized upon standing. The solid was subsequently dried overnight under vacuum at 50° C. to give crude amine 3 (39.5 g, 97%) as a solid, pale brown residue.

a3) Synthesis of $N^1,N^4$-(bis4-(4-methylpiperazine-1-carbonyl)phenyl)-terephthalamide An oven dried 1000 mL 3-necked flask was equipped with a mechanical stirrer, nitrogen in- and outlet and cooled to room temperature under a nitrogen flow. Amine 3 (38.1 g, 173 mmol) was put in the flask and dissolved in dry N-methylpyrollidin-2-one (NMP) (503 g). The solution was cooled for 20 minutes in an ice-water bath after which solid terephthaloyl dichloride flakes (17.53 g, 86.3 mmol, 0.50 eq) were added to the flask in a single portion while stirring at 500 rpm. The addition funnel was rinsed with NMP (40 g) and the suspension was stirred for 1 h at 0° C. followed and 0.5 h at room temperature. Concentrated aqueous ammonium hydroxide (94 g, 30 w %) was slowly added to the reaction mixture which was subsequently poored into demineralized water (3.5 L). The pH of the solution was adjusted to 10 by addition of more ammonium hydroxide solution (130 g, 30 w %). The fine, white precipitate was allowed to settle for about 0.5 hour after which the clear top layer was decanted. The precipitate was suspended, filtered over a Millipore filter (Durapore GV, 0.22 μm pore size) while applying vacuum and washed with demineralized water (3×250 mL). The crude product was further purified by repetitive (4×) suspension of the product in warm, high-purity MilliQ water (1.0 L, T=65° C.) for about 1 hour, cooling to approximately 36-38° C., filtration over a Millipore filter, washing with MilliQ water (2×250 mL) and drying to the air under suction for 5-15 minutes. The wet product was dried overnight under vacuum at 50° C. to give the desired compound as an off-white, fine powder (46.4 g, 95%).

b) Synthesis of 1-methyl-4-[4-(4-methylpiperazine-1-carbonyl)benzoyl]piperazine

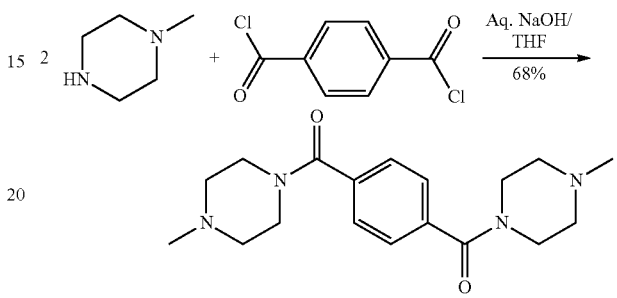

A 500 mL three-necked flask was equipped with a mechanical stirrer and an addition funnel. The flask was charged with a solution of N-methylpiperazine (26.58 g, 0.265 mol) in 2.0 M NaOH (166.2 g, 0.308 mmol NaOH). The flask was cooled for 30 minutes in an ice/water bath while stirring. Then, a solution of terephthaloyl dichloride (24.36 g, 0.120 mol) in dry tetrahydrofuran (55.2 g) was added in a dropwise manner to the flask while vigorously stirring. The rate of addition was such that the internal temperature remained below 5° C. The reaction mixture was diluted by addition of demineralized water and the pH was set to 8 by careful addition of 37 w % HCl solution. The reaction mixture was split into two equal portions. The product was isolated from each portion of the reaction mixture by extraction with dichloromethane (2×400 mL+3× 100 mL). The combined organic layers were washed with brine and dried over $Na_2SO_4$. After filtration, all volatiles were removed under reduced pressure on a rotary evaporator and the crude product was purified further by trituration in diethyl ether followed by drying under vacuum to give the title compound as a fine white powder (27.16 g, 68%)

5. Spinning of an Aramid Fiber According to the Invention i) Preparation of a Sandy Spin Dope Batches of sandy spindope were prepared in a 6 liter Drais mixer. First, 2008 g of 99.8 wt % sulfuric acid was mixed with 15 g aromatic additive for 2 hours at −20° C. Then 477 g poly(p-phenylene terephthalamide) (PPTA) was added and mixed for 2 hours. Subsequently, cooling was stopped and the mixture was stirred for an additional 10-12 hours. The resulting sandy spin dope contained 19.1 wt % PPTA and 0.6 wt % additive. A reference batch of 19.7 wt % PPTA was prepared in a comparable way, but without addition of additive to the sulfuric acid. The total solid content in both spin dopes was 19.7 wt % ii) Spinning of the Dope

The sandy spin dopes obtained from i) were dosed to a double screw extruder and extruded at 85° C., leading to a molten liquid crystalline solution. This solution was pumped through a spinneret with 106 holes of 59 micron diameter. After extrusion through the spinning holes the liquid filaments were drawn in an air gap of about 5 mm, and subsequently entered a coagulation bath consisting of demineralized water. The coagulated fibers were washed with additional water to remove residual sulfuric acid, neutralized with NaOH solution, washed with additional water, dried at 250° C. or 160° C. and wound on bobbins. The whole spinning process was conducted online at 160 m/min winding speed.

Example 1

Aramid Shaped Bodies According to the Invention

Sample 1

Spindope containing 19.1 wt % para-aramid and 0.6 wt % $N^1,N^4$-bis[4-(4-methylpiperazine-1-carbonyl)phenyl] benzene-1,4-dicarboxamide (based on the weight of the spin dope) was prepared and processed as described above, the yarn was dried at 250° C.

Comparative Sample 1

Spindope containing 19.7 wt % para-aramid was prepared and processed as mentioned above, no aromatic compound was added, the yarn was dried at 250° C.

Subsequently, the hydrolytic stability t0.9 and t0.8 of the fibers prepared as sample 1 and comparative sample 1 was tested as described. The results are shown in Table 1.

TABLE 1

| | hydrolytic stability of comparative sample 1 and sample 1 (according to the invention) | | | | |
|---|---|---|---|---|---|
| sample | additive (wt %, based on fiber weight) | linear density (dtex) | strength (mN/tex) | modulus (GPa) | hydro stab. t0.9 (weeks) | hydro stab. t0.8 (weeks) |
| 1 | 2.8 | 181 | 2326 | 112 | 8 | 23 |
| comp. 1 | — | 177 | 2289 | 109 | 2 | 10 |

Hydro stab: hydrolytic stability, determined as described, weight percentage of additive is based on the weight of the fiber.

The hydrolytic stability t0.9 and t0.8 of the fibers comprising the additive is improved greatly, from 2 to 8 weeks and from 10 to 23 weeks, respectively. This means that polyarylene shaped bodies according to the invention retain their strength much longer than conventional polyarylene fibers and can therefore be used much longer under hydrolysis-inducing conditions.

The modulus of the polyarylene fiber can be improved by an offline heat treatment. To determine this, the following samples have been prepared:

Sample 2

Fibers were spun as in sample 1 but dried at 160° C. instead of 250° C.

Comparative Sample 2

Fibers were spun as in comparative sample 1 but dried at 160° C. instead of 250° C.

Sample 3

The fibers of sample 2 were heat-treated at 400° C. under 1.6 cN/dtex tension in zone 1, and 120° C. under 0.11cN/dtex tension in zone 2.

Sample 4

The fibers of sample 1 were heat-treated at 450° C. under 1.5 cN/dtex tension in zone 1, and 120° C. under 0.11 cN/dtex tension in zone 2.

TABLE 2

| | Heat treatment results | | | | |
|---|---|---|---|---|---|
| sample | additive (wt %) | Heat treatment (° C.) | linear density (dtex) | strength (mN/tex) | modulus (GPa) | crystal size L110 (Å) |
| 2 | 2.8 | — | 181 | 2305 | 91 | 52 |
| 3 | 2.8 | 400 | 173 | 2091 | 127 | 87 |
| 4 | 2.8 | 450 | 172 | 1800 | 131 | 103 |
| comp. 2 | — | — | 177 | 2232 | 90 | 53 |

The invention claimed is:
1. A polyarylene fiber comprising 0.1-15% based on the weight of the fiber of an aromatic compound or a combination of aromatic compounds wherein each aromatic compound comprises an aromatic core and at least one of the substituents A or B, where A is represented by formula 1

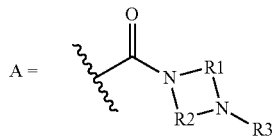

and B is represented by formula 2

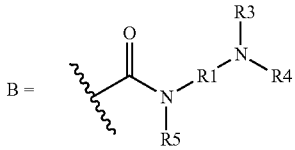

wherein R1 and R2 are independently of each other selected from an alkanediyl comprising 2 to 10 carbon atoms;
wherein R3 and R4 are independently of each other selected from —H, alkyl comprising 1 to 10 carbon atoms, homocycloalkyl comprising 3 to 10 carbon atoms or heterocycloalkyl comprising 1 to 10 carbon atoms;
wherein R5 is selected from: —H, alkyl comprising 1 to 10 carbon atoms, homocycloalkyl comprising 3 to 10 carbon atoms, heterocycloalkyl comprising 1 to 10 carbon atoms, or a carbonyl which forms a phthalimido ring structure fused to the aromatic core.
2. The polyarylene fiber according to claim 1 wherein the polyarylene is a lyotropic liquid crystal polymer.
3. The polyarylene fiber according to claim 1 wherein the at least one aromatic compound has an aromatic core selected from: Core 1 (formula 3), Core 2 (formula 4) or Core 3 (formula 5)

Core 1

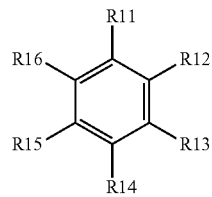

Formula 3

-continued

Core 2

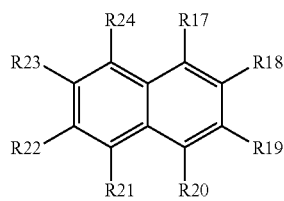

Formula 4

Core 3

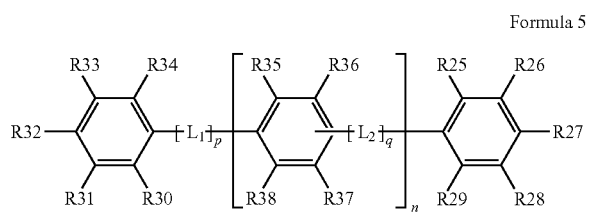

Formula 5 wherein R11, R12, R13, R14, R15, R16, R17, R18, R19, R20, R21, R22, R23, R24, R25, R26, R27, R28, R29, R30, R31, R32, R33, R34, R35, R36, R37 and R38 are independently of each other selected from the following monovalent radicals: an additional substituent A or B, —H, halogen, $NO_2$, CN, $OR_3$, —$NR_3R_4$, $SR_3$, alkyl comprising 1 to 10 carbon atoms, homocycloalkyl comprising 3 to 10 carbon atoms, heterocycloalkyl comprising 1 to 10 carbon atoms, perfluoroalkyl comprising 1 to 10 carbon atoms and an optionally substituted carbonyl;

wherein L1 and L2 are each independently of each other selected from the following bi- and trivalent radicals: carbonyl, —O—, —S—, —$SO_2$—, alkanediyl comprising 1 to 6 carbon atoms, perfluoroalkanediyl comprising 1 to 6 carbon atoms, cycloalkanediyl comprising 3 to 10 carbon atoms, perfluorocycloalkanediyl comprising 3 to 10 carbon atoms, iminocarbonyl, acyloxy; and wherein p and q are 0 or 1 and n is 0, 1, 2, or 3.

4. The polyarylene fiber according to claim 1 wherein the at least one aromatic compound is substituted with at least one substituent A wherein R1 and R2 of A are —$C_2H_4$—.

5. The polyarylene fiber according to claim 1 wherein the at least one aromatic compound is substituted with at least one substituent A wherein R3 of A is methyl.

6. The polyarylene fiber according to claim 1 wherein the at least one aromatic compound is substituted with at least one substituent B wherein R1 of B is —$C_2H_4$—.

7. The polyarylene fiber according to claim 1 wherein the at least one aromatic compound is substituted with at least one substituent B wherein R3 and R4 of B are methyl.

8. The polyarylene fiber according to claim 1 wherein the at least one aromatic compound is substituted with at least one substituent B wherein R5 of B is H.

9. The polyarylene fiber according to claim 3 wherein the at least one aromatic compound which comprises Core 3 and wherein L1 and L2 are each an iminocarbonyl group where n, p and q are 1.

10. The polyarylene fiber according to claim 1 wherein the at least one aromatic compound comprises A which is a carboxamide derived from 1-alkyl-piperazine.

11. The polyarylene fiber according to claim 1 wherein the at least one aromatic compound comprises B which is carboxamide derived from an N,N-dialkylethylenediamine.

12. The polyarylene fiber according to claim 1 wherein the molecular weight of each aromatic compound is between 200 and 1000 g/mol.

13. The polyarylene fiber according to claim 1 wherein the polyarylene fiber has a hydrolytic stability t0.9 of at least 3 weeks, wherein the hydrolytic stability t0.9 is defined as the period of time until the breaking tenacity of the fiber when being exposed to a solution of pH 4 and 90° C. amounts to 90% compared to the breaking tenacity of the fiber when being exposed to air having a temperature of 20° C. and 65% relative humidity.

14. A spin dope comprising polyarylene polymer and 0.1 to 15% based on the weight of polyarylene in the spin dope of an aromatic compound or a combination of aromatic compounds, wherein each compound comprises an aromatic core and at least one of the substituents A or B, where A is represented by formula 1

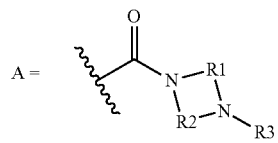

and B is represented by formula 2

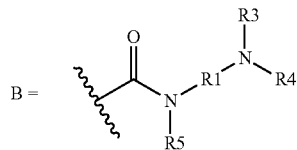

wherein R1 and R2 are independently of each other selected from an alkanediyl comprising 2 to 10 carbon atoms;
wherein R3 and R4 are independently of each other selected from —H, alkyl comprising 1 to 10 carbon atoms, homocycloalkyl comprising 3 to 10 carbon atoms or heterocycloalkyl comprising 1 to 10 carbon atoms;
wherein R5 is selected from: —H, alkyl comprising 1 to 10 carbon atoms, homocycloalkyl comprising 3 to 10 carbon atoms, heterocycloalkyl comprising 1 to 10 carbon atoms, or a carbonyl which forms a phthalimido ring structure fused to the aromatic core.

15. A process to manufacture a polyarylene fiber with improved hydrolytic stability comprising the steps:
i) preparing a composition comprising polyarylene polymer, a solvent and a compound or combination of compounds,
ii) processing the composition to obtain the polyarylene fiber, wherein each compound comprises an aromatic core and at least one of the substituents A or B, where A is represented by formula 1

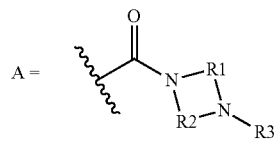

and B is represented by formula 2

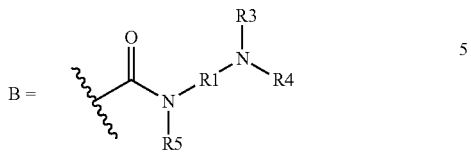

wherein R1 and R2 are independently of each other selected from an alkanediyl comprising 2 to 10 carbon atoms;

wherein R3 and R4 are independently of each other selected from —H, alkyl comprising 1 to 10 carbon atoms, homocycloalkyl comprising 3 to 10 carbon atoms or heterocycloalkyl comprising 1 to 10 carbon atoms;

wherein R5 is selected from: —H, alkyl comprising 1 to 10 carbon atoms, homocycloalkyl comprising 3 to 10 carbon atoms, heterocycloalkyl comprising 1 to 10 carbon atoms, or a carbonyl which forms a phthalimido ring structure fused to the aromatic core.

* * * * *